United States Patent
Tseng et al.

(10) Patent No.: US 11,426,346 B2
(45) Date of Patent: Aug. 30, 2022

(54) LUTEIN-CONTAINING OPHTHALMIC COMPOSITION

(71) Applicant: Taipei Medical University, Taipei (TW)

(72) Inventors: Ching-Li Tseng, Taipei (TW); I-Chan Lin, Taipei (TW); Yi-Zhou Chen, Taipei (TW); Yu-Lun Chuang, Taipei (TW); Cheng-Han Tsai, Taipei (TW); Zhi-Yu Chen, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 184 days.

(21) Appl. No.: 16/600,553

(22) Filed: Oct. 13, 2019

(65) Prior Publication Data
US 2020/0222316 A1 Jul. 16, 2020

(30) Foreign Application Priority Data
Jan. 16, 2019 (TW) ................................. 108101637

(51) Int. Cl.
| | |
|---|---|
| *A61K 9/00* | (2006.01) |
| *A61K 31/047* | (2006.01) |
| *A61K 33/14* | (2006.01) |
| *A61K 33/42* | (2006.01) |
| *A61K 47/32* | (2006.01) |
| *A61P 27/04* | (2006.01) |

(52) U.S. Cl.
CPC .......... *A61K 9/0048* (2013.01); *A61K 31/047* (2013.01); *A61K 33/14* (2013.01); *A61K 33/42* (2013.01); *A61P 27/04* (2018.01)

(58) Field of Classification Search
None
See application file for complete search history.

(56) References Cited

U.S. PATENT DOCUMENTS

2005/0202097 A1* 9/2005 Maskin ................... A61P 37/06
424/524
2010/0226999 A1* 9/2010 Quevillon-Coleman ....................
A61K 47/183
424/616

FOREIGN PATENT DOCUMENTS

WO WO-2009084069 A2 * 7/2009 ............. A61K 9/127

OTHER PUBLICATIONS

Neelam et al., Putative protective role of lutein and zeaxanthin in diabetic retinopathy, Br J Ophthalmol May 2017;101(5):551-558, printed from https://pubmed.ncbi.nlm.nih.gov/28232380/, Abstract only, 2 pages.*

* cited by examiner

*Primary Examiner* — Gigi G Huang
(74) *Attorney, Agent, or Firm* — Amin, Turocy & Watson, LLP

(57) ABSTRACT

A lutein-containing ophthalmic composition, wherein the ophthalmic composition is mainly consisting of a natural anti-inflammatory substance, a substance with increasing liquid viscosity, and an artificial tear. The substance with increasing liquid viscosity could apply the ophthalmic composition to elongate the retention time on the ocular surface, thereby increasing the retention time of anti-inflammatory substance on the ocular surface for treating dry eye syndrome and inhibiting ocular surface inflammation.

9 Claims, 7 Drawing Sheets
(1 of 7 Drawing Sheet(s) Filed in Color)

LUTEIN-CONTAINING OPHTHALMIC COMPOSITION

BACKGROUND OF THE INVENTION

1. Field of the Invention

The present disclosure relates to a lutein-containing and anti-inflammatory effect ophthalmic composition, wherein the ophthalmic composition is used for inhibiting the inflammation of the ocular surface and relief the symptom of dry eye syndrome.

2. Description of the Prior Arts

The human eye is a spherical structure, and the structure from the outside to the inside is sequentially tear film, conjunctiva, cornea, anterior chamber, iris, lens, vitreous body, and retina, wherein the lens as a central demarcation line, and the eyeball is divided into an anterior part and a posterior part. The tear film, cornea, and conjunctiva at the anterior part of the eye as first ocular surface for protecting eyeball and contacting outside. There are various inflammatory reactions at the anterior part in unhealthy condition.

The tear film is divided into three layers from the inside to the outside as a mucin layer, an aqueous layer and a lipid layer. The function of the tear film is keeping moist surface, providing nutrients to the cornea, and removing foreign objects to protect ocular surface. If one of the layers in tear film is abnormal or functional incapacitation, such as the dysfunction of the lipid layer, and the abnormal function of the mucin layer for tear excessively evapotranspiration or decreasing amount tears of the aqueous layer, which causes the osmolarity change of tears and also resulted in chronic inflammation on the ocular surface, and then resulting in dry eye syndrome (DES) eventually.

Dry eye syndrome is a disease due to tear secretion changes, abnormal cornea, conjunctiva and lacrimal gland dysfunction. Long-term using electrical products (computer, mobile device), wearing contact lens, and staying in an air-conditioned room would result in drying condition on the ocular surface, which induces chronic inflammation and leads to the so-called dry eye syndrome eventually.

Dry eye syndrome usually causes ocular dryness, hyperemia, ocular irritation, and accompanied by inflammatory condition of the ocular surface, it can cause many discomforts in patient's life. If dry eye syndrome is not treated properly, it could even lead to corneal ulceration, turbidity, and then resulting in vision impair and inability to recover. The treatment of dry eye syndrome nowadays is usually using artificial tear (AT), and anti-inflammatory drugs serially. However, the artificial tear dropped to the eye will be quickly removed via the nasolacrimal duct due to the special ocular anatomy, resulting in artificial tears staying on the surface of the eye for a short time. Moreover, one AT dosing, then comes the anti-inflammatory agent dosing usually need to have a time interval (5-10 minutes) for these two agents via topical delivery, eye drops. Patients usually forgotten the second one due to busy life, and then cause delayed therapeutic effect and prolongs curative time. Furthermore, anti-inflammatory drugs are usually creamy that patients may suffer vision blurred and meet difficulty in mobility when dosing.

Anti-inflammatory agents in ophthalmology commonly used for the dry eye syndrome treatment can be divided into two categories: one is steroids and the other is non-steroidal anti-inflammation drug (NSAID). After long-term use of anti-inflammatory drugs containing steroids, it could block the tear drainage, further increase the intraocular pressure, optic nerve atrophy, and finally resulted in glaucoma blindness. There are some drawbacks of non-steroidal anti-inflammation drugs, such as bromfenac and cyclosporine A. Bromfenac would induce side effects such as photophobia, eye irritation, and even thinning of the cornea. Cyclosporine A, a hydrophobic agent dissolved in oil base, could cause burning, congestion, and itching of the eyes. Therefore, the development of an anti-inflammatory drug with no or low side effects and it's also comfortable for patients using are the main subjects of research development for the ophthalmological pharmaceutical industry.

The human retina contains a variety of carotenoids, and lutein is one of the main compositions in retina. Lutein is an anti-inflammatory and anti-oxidant substance conduced to protect the visual nerve cells by absorbing harmful blue light and near-ultraviolet light directly. Its antioxidant capacity can reduce the free radical's formation in the visual receptor and retinal pigment epithelium (RPE) to protect the macula, and then provide the clearest vision.

Neither carotenoids nor lutein are synthesized by human beings themselves, they can only be supplemented by ingesting food or health food; there are a large amount of lutein contained in green vegetables or egg yolk. However, lutein supplemented by food ingestion needs to pass through the intestinal absorption and blood circulation system, and then finally enters the blood terminal organ "eye". The blood-retina barriers are a strong barrier to overcome for drug delivery from circulation to the eye; therefore, lutein acquired from food supplement, its bioavailability is very low in retina.

Polyvinyl alcohol (PVA) is a synthetic polymer characterized by low protein adsorption, good biocompatibility, high hydrophilicity and chemical resistance. Depending on the molecular weight, it has different characteristics, such as increasing its molecular weight to increase viscosity, adhesion, strengthening tension, water resistance and gelation; reducing molecular weight will increase the water solubility of PVA. Because of its versatile physical characteristics, it is widely used in various fields.

In view of the lack of the prior art, the Applicant has invented an ophthalmic composition, which has a natural anti-inflammatory component and viscosity enhancer to increase the retention time of drugs on the ocular surface for reducing the administering times effectively, further relief the inflammatory condition in eye.

SUMMARY OF THE INVENTION

The object of the present invention is to provide a lutein-containing ophthalmic composition, wherein the lutein can be administered directly to the ocular surface for increasing the concentration of the lutein on the ocular surface, and further inhibiting ocular surface inflammation or treating dry eye syndrome effectively. The present invention can overcome the fact that lutein is food by oral ingestion with very low applicability on the ocular surface.

To achieve the above objective, the technical means of the present invention is that the ophthalmic composition is consisting of a natural substance with anti-inflammatory effect such as lutein, a substance with increasing liquid viscosity such as polyvinyl alcohol (PVA) and artificial tears. The ophthalmic composition comprising lutein with anti-inflammatory effect could apply to the ocular surface directly.

In another aspect, the object of the present invention is to provide an ophthalmic composition for prolonging the retention time on the ocular surface, thereby increasing the retention time of anti-inflammatory substances or therapeutic drugs on the ocular surface for treating or inhibiting dry eye syndrome effectively.

To achieve the above objective, the technical means of the present invention is the ophthalmic composition comprising a substance for increasing the viscosity of the liquid. For example, the ophthalmic composition comprising polyvinyl alcohol (PVA) can elongate the retention time on the ocular surface, and the then lutein can also infiltrate into the posterior part of the eye. Therefore, in addition to treating the dry eye syndrome and inhibiting the inflammation of the ocular surface, the ophthalmic composition of the present invention can protect retina and prevent retinopathy.

BRIEF DESCRIPTION OF THE DRAWINGS

The application file contains at least one drawings executed in color. Copies of this patent or patent application publication with color drawing(s) will be provided by the Office upon request and payment of the necessary fee.

DETAILED DESCRIPTION OF THE PREFERRED EMBODIMENTS

In order to facilitate the examiner to have a further understanding of the lutein-containing ophthalmic composition in the present invention, the embodiments are combined with the drawings, and the details are as follows.

EXAMPLE 1

This example provided an ophthalmic composition consisting of a natural anti-inflammatory substance and a viscoelastic enhancer which increases the liquid viscosity. This example was to determine whether the ophthalmic composition has adverse effects, causes damage on human corneal epithelial cells (HCE-2), and can it used to reduce the inflammatory response on inflamed HCE-2cells.

In this example, the natural anti-inflammatory substance was the lutein (abbreviated L), and the substance to increase the liquid viscosity was the polyvinyl alcohol (abbreviated PVA).

A routine maintenance of human corneal epithelial cells (HCE-2) is described as follow: 1 mL FNC coating Mix aqueous solution was added to the 10 cm culture dish before seeding human corneal epithelial cells (HCE-2), and then removed the remaining FNC aqueous solution after 30 seconds. After then, HCE-2 cells were defrosted at 37° C. water tank for culturing, and subculturing at a ratio of 1:3 to 1:4; the KSFM culture medium was changed every three days.

Cytotoxicity Test

In this test, a 96-well plate was coated with 200 μL/well FNC coating MIX aqueous solution. After 30 seconds, $5 \times 10^3$ HCE-2 cells were seeded per well, and cultured with KSFM culture medium. After the next day, the KSFM culture medium was removed and rinsed with PBS buffer, followed by a final concentration of 10 μM, 5 μM, 2.5 μM, 0.125 μM of lutein (L) were mixed with 1%, 0.5%, 0.1%, 0.05%, 0.01% (wt./v) of polyvinyl alcohol (PVA) respectively, and then added to a 96-well plate and cultured with HCE-2 cells. The next day, the WST-8 reagent and KSFM medium were mixed at a volume ratio of 1:10. The cultured medium was removed, and 110 μL of the culture medium mixed with the reagent was added to each well, and the reaction was carried out in an incubator for 3.5 hours, and the absorbance of medium was detected by an ELISA reader at 450 nm, and finally analyzed by ANOVA (Analysis of Variance) test. The control group was only cultured in the KSFM medium.

Figure 1:
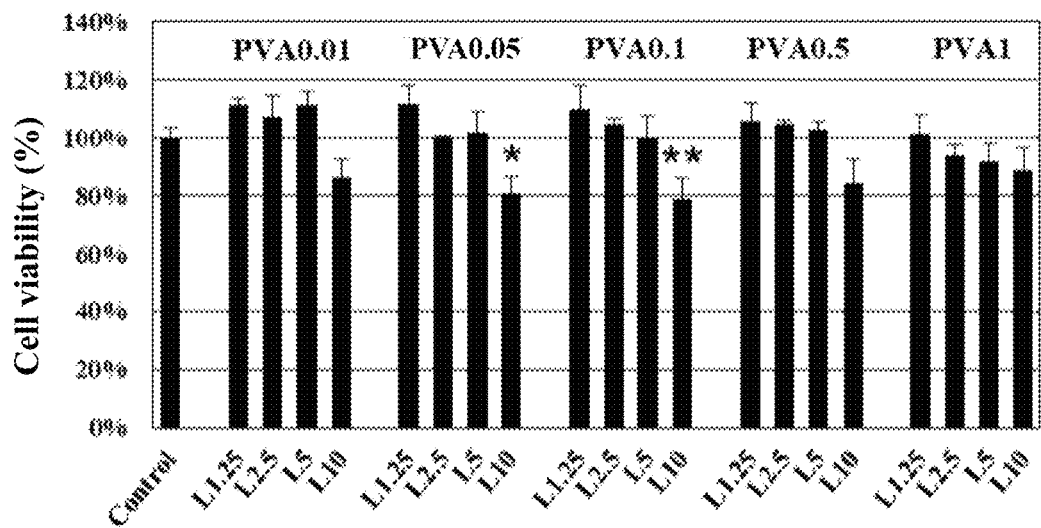
FIG. 1 The cytotoxicity test of the ophthalmic composition of the present invention.

As shown in FIG. 1, when lutein (L) and polyvinyl alcohol (PVA) were mixed, there was no significant difference at low concentration (<5 μM) compared with the control group.

Cellular Activity Assay

This example was performed using a Live/Dead staining for cell activity assay. 0.5 mL of FNC coating MIX aqueous solution was coated in a 24-well plate and removed after 30 seconds. $3 \times 10^4$ HCE-2 cells were seeded in each well. After the next day, lutein (L) was added in the culture medium at the final concentration of 20 μM, 10 μM, or 5 μM; and with/without mixed 1% (wt./v) polyvinyl alcohol (PVA). After the next day and the third day, the culture medium was removed. 0.5 mL of a mixture of 2: 1: 2000 Calcein-AM, propidium iodide (PI) and serum-free medium were added to the 24-well plate, and then placed in a 37° C. incubator for 10 minutes. The cells were observed and photographed by an inverted fluorescent microscope. In the death control group, Triton X-100 with 0.5% (wt./v) final concentration was added to the cells before the culture medium was removed, and finally ANOVA test was used for data analysis. The control group was only cultured in the KSFM medium.

Figure 2:
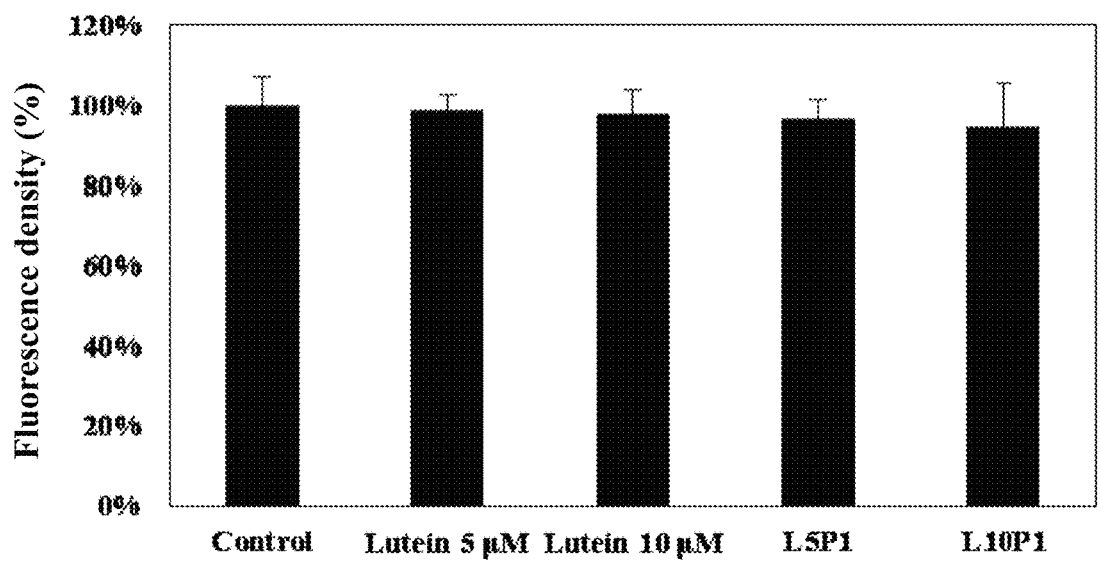
FIG. 2 The quantification of live/dead staining of cell activity test of the ophthalmic composition of the present invention.

As shown in FIG. 2, the figure was quantified from the fluorescence staining results of cell viability. When lutein (L) was mixed with polyvinyl alcohol (PVA), there was no significant difference between the control group and the green fluorescence group of lutein (L) at a concentration of 5 μM (L5P1) and 10 μM (L10P1), and no red fluorescence of dead cells was observed, indicating that on the first day, lutein (L) mixed with polyvinyl alcohol (PVA) had no effect on cell activity.

Gene Expression of Inflammatory Cytokines $3 \times 10^5$ (cell/ml) human corneal epithelial cells (HCE-2) were cultured in a 6-well plate and cultured overnight in an incubator for cell attachment, followed 500 ng/mL lipopolysaccharides (LPS) was added in culture medium for co-cultured with cells for 6 hours to induce cell inflammation. After 6 hours, the medium containing lipopolysaccharide (LPS) was removed, and the medium with the lutein, PVA was added to a 6-well plate. After 2 hours of treatment, the gene expressions of cellular inflammatory cytokines (IL-1β, IL-6, TNF-α) were detected by real-time polymerase chain reaction (Real-Time PCR). The cells cultured in medium comprise a control group (normal cells), the LPS group, and variant experimental groups were listed as follows:

Control group: normal HCE-2 cells culture in medium, and no drug was added to the medium.
LPS group: cellular inflammation was induced by lipopolysaccharide (LPS), and no drug was added to the medium.
PVA1 group: 1% (wt./v) polyvinyl alcohol (PVA) was added to the medium.
L2.5 group: 2.5 μM lutein (L) was added to the medium.
L5 group: 5 μM lutein (L) was added to the medium.
L10 group: 10 μM lutein (L) was added to the medium.
L2.5P1 group: 2.5 μM lutein (L) and 1% (wt./v) polyvinyl alcohol (PVA) were added to the medium.
L5P1 group: 5 μM lutein (L) and 1% (wt./v) polyvinyl alcohol (PVA) were added to the medium.
L10P1 group: 10 μM lutein (L) and 1% (wt./v) polyvinyl alcohol (PVA) were added to the medium.

Figure 3A:
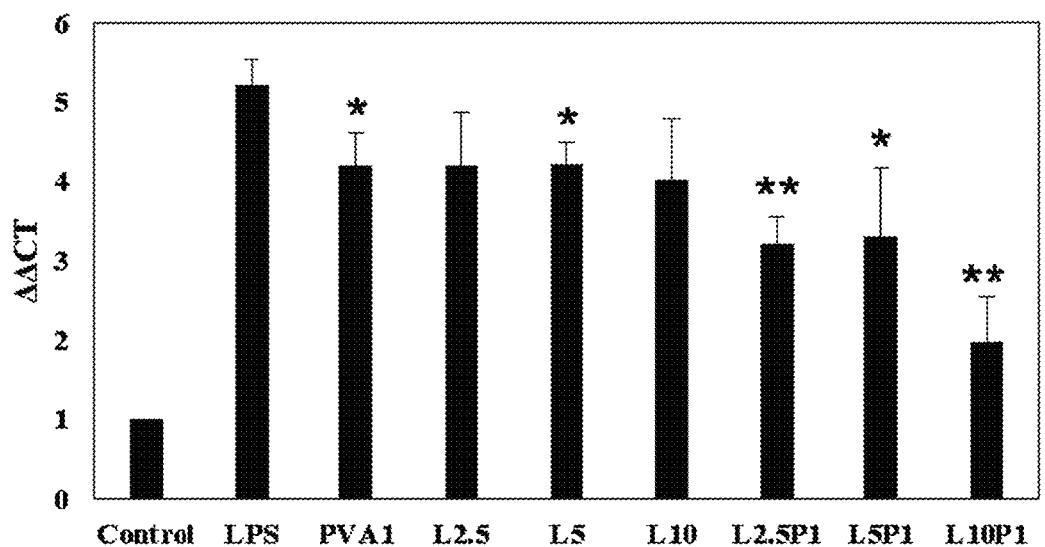
FIG. 3A The amount of the gene expression of the inflammatory cytokine IL-1β of the corneal epithelium cells of the ophthalmic composition of the present invention.
Figure 3B:
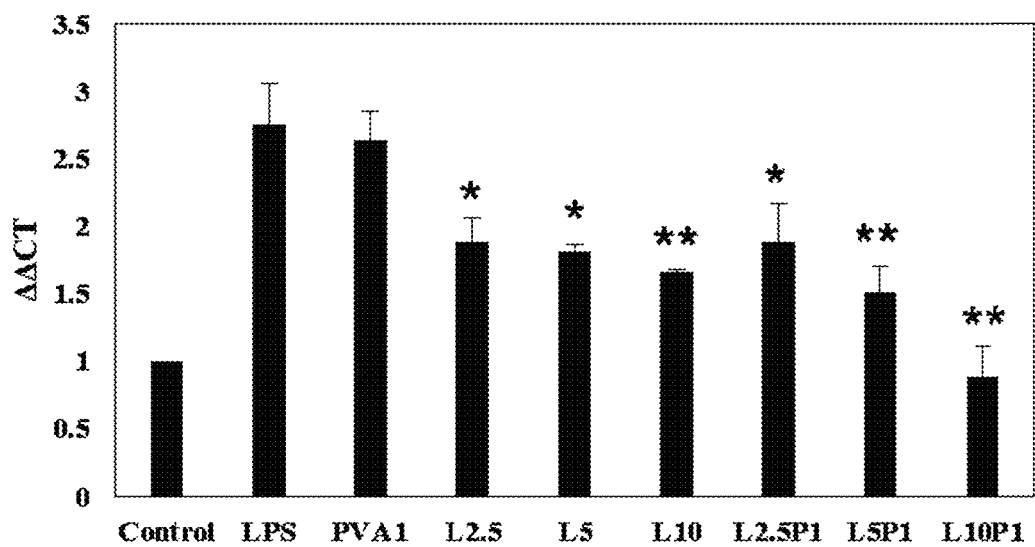
FIG. 3B The amount of the gene expression of the inflammatory cytokine IL-6 of the corneal epithelium cells of the ophthalmic composition of the present invention.
Figure 3C:
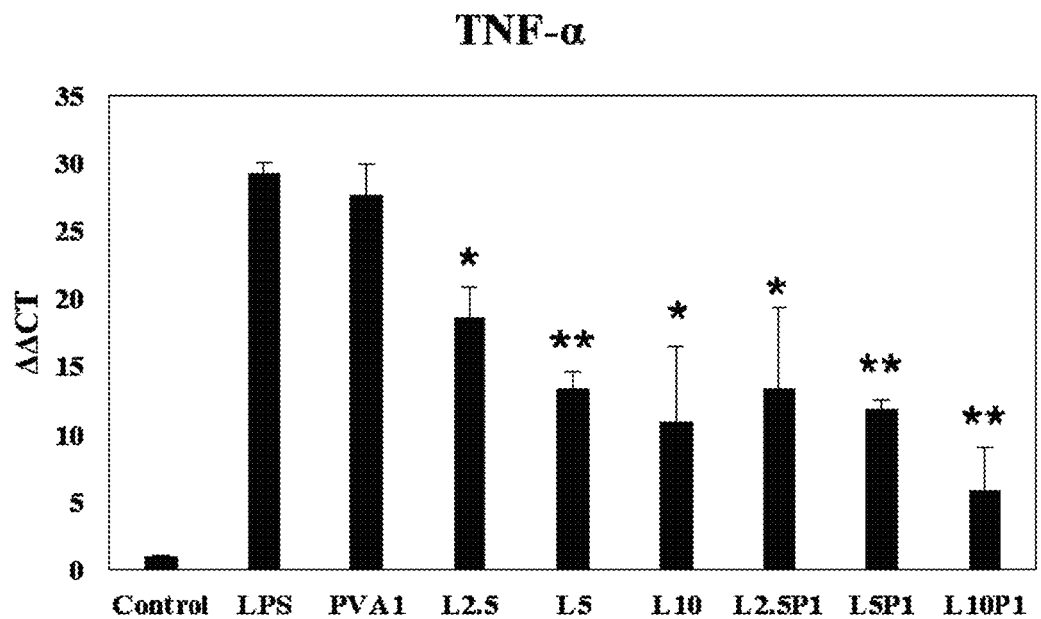
FIG. 3C The amount of the gene expression of the inflammatory cytokine TNF-α of the corneal epithelium cells of the ophthalmic composition of the present invention.

As shown in FIGS. 3A to 3C, after co-cultivation with human corneal epithelial cells (HCE-2) and 500 ng/mL LPS for 6 hours, the gene expression of cellular inflammatory cytokines of the LPS group was increased significantly compared to the control group, indicating that HCE-2 cells were successfully induced to inflammation. Then, after 2 hours treatment with different drugs, the expression of IL-1β was decreased, but the IL-6 and TNF-α had no significantly inhibitory effect in PVA1 group.

With the lutein (L) concentration increased, lutein (L) has anti-inflammatory ability to inhibit the expression of inflammatory cytokines (e.g. IL-1β, IL-6 or TNF-α) of LPS-induced inflammation of human corneal epithelial cells (HCE-2). At the same time, it could also be observed that the lutein (L) mixed polyvinyl alcohol (PVA) 1% (wt./v) group (L10P1), compared with the LPS induced inflammation group, could inhibit the inflammatory cytokines significantly. (*: $p<0.05$, : $p<0.01$, *: $p<0.001$)

According to the results of this examination, lutein concentration at 2.5 μM to 10 μM mixed with 1% (wt./v) polyvinyl alcohol (PVA) did not harmful to human corneal epithelial cells (HCE-2) and has the best anti-inflammatory effect.

The WST-8, enzyme linked immunosorbent assay (ELISA), Live/Dead staining and Real-Time PCR were experimental kits and conventional techniques in the biomedical field, therefore, they were not described in the specification here.

EXAMPLE 2

Based on the results of Example 1, the 1% (wt./v) polyvinyl alcohol (PVA) and 2.5 μM to 10 μM lutein (L) was added to artificial tears (AT) to figure out whether the physiological characteristics of artificial tears, such as pH, osmotic pressure, viscosity and refractive index are suitable for ophthalmic application.

The artificial tear (AT) was a conventional artificial tear solution, and its physiological characteristics were similar to those of human tears, including: 450 mg sodium chloride (NaCl), 150 mg potassium chloride (KCl), 15 mg calcium chloride ($CaCl_2$), 450 mg disodium hydrogen phosphate ($Na_2HPO_4$).

In this example, the brand of the pH meter is EUTECH INSTRUMENTS model (pH510); the brand of the micro osmometer is Advanced Instruments model number (3320); the brand of the program rheometer device (detecting viscosity) is Brookfield (DVIII); the brand of the flexometer is ATAGO (DR-A1 standard).

The results were shown in Table 1. After the polyvinyl alcohol (PVA) and lutein (L) were added to artificial tears (AT), the physiological characteristics were similar to those of the conventional artificial tears. The pH of the normal human tear fluid was 6.5-7.6, and the osmotic pressure was 260-340 mOsm/kg. The physiological characteristics of the ophthalmic composition of the present invention were also similar to those of normal human tears.

TABLE 1

Comparison of physiological characteristics of ophthalmic composition

|  | pH | osmotic pressure (mOsm/kg) | viscosity (pa · s) | refractive index (m · sl/(m · sl)l) |
|---|---|---|---|---|
| artificial tears (AT) | 8.3 | 253 | 0.9 | 1.33~134 |
| ophthalmic composition (this invention) | 7.7~8.3 | 260~280 | 1.15 | 1.334 |

The pH meter, the micro osmometer, and the program rheometer device were experimental instruments and were common techniques, and thus were not described in the specification.

EXAMPLE 3

This example provides an ophthalmic composition consisting of the anti-inflammatory substance lutein (L), the polyvinyl alcohol (PVA) to increase the liquid viscosity, and the artificial tear of Example 2. The therapeutic efficacy test of the ophthalmic composition was used to treat dry eye syndrome.

The concentration of the lutein (L) was used in a range of 2.5 μM to 10 μM, and further was used in a concentration range of 0.5 μM to 15 μM. The concentration of polyvinyl alcohol (PVA) was used in an amount of 0.1% to 5% (wt./v). In this example, the concentration of lutein was 5 μM, and the concentration of polyvinyl alcohol (PVA) was 1% (wt./v), L5P1.

Experimental Procedure for the Dry Eye Syndrome in Animal

In the animal study, C57BL/6J male mice were used and divided into 5 groups (4 mice in each group), and 0.1% benzalkonium chloride (BAC) was dripped onto the surface of mice eyes twice a day for 13 days to induce inflammation of the ocular surface, resulting in developing dry eye syndrome, and then treated with different drugs according to the groups. After 10 days' treatment, corneal fluorescence staining and tear secretion test were performed. The control and experimental groups were shown in Table 2, see as below.

TABLE 2

The description of variant experimental groups in dry eye syndrome animal study

| Group | Description |
|---|---|
| Control' group | Normal mice with no dry eye syndrome, and no therapeutic drug administered |
| DES group | Mice with dry eye syndrome induced by 0.1% BAC |
| AT group | Mice with dry eye syndrome treated with artificial tears |
| L5' group | Mice with dry eye syndrome treated with 5 µM lutein (L) |
| L5P1' group | Mice with dry eye syndrome treated with 5 µM lutein (L) and 1%(wt./v) PVA |

The Drug Retention on Animal Ocular Surface

In this example, the artificial tear group (AT), the L5' group and the L5P1' group were tested. In abovesaid three groups of mice, 2 µL 5-(and-6)-carboxytetramethylrhodamine succinimidyl ester (TAMRA) with a final concentration of 100 µg/mL was dropped onto the ocular surface for fluorescence observation. The Non-Invasion In Vivo Image System (IVIS) was used to observe and quantify the fluorescent dye retention on the ocular surface of artificial tears with the three different components.

Figure 4:
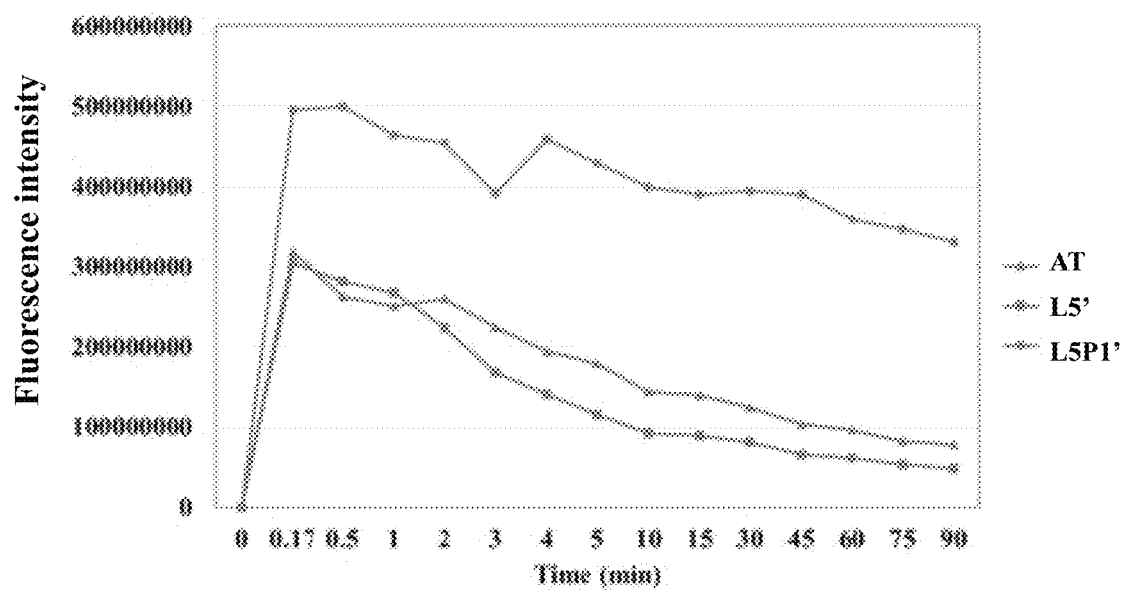
FIG. 4 The quantification diagram of the fluorescence intensity on eyes from the ophthalmic composition of the present invention for applying to the ocular surface in mice.

As shown in FIG. 4, the ophthalmic composition of the L5P1'group could prolong the dye retention on the ocular surface due to the viscosity of the L5P1' group was increased by the addition of the polyvinyl alcohol (PVA). This can reduce the frequency of repeated doses, and shorten the treatment period for treating the ocular surface inflammation and dry eye syndrome. Prolonging the retention time of the ophthalmic composition could increase the chance of the lutein (L) penetrating into the posterior eye, further preventing retinopathy and enhancing protection of the retina.

Corneal Fluorescent Staining

Figure 5:
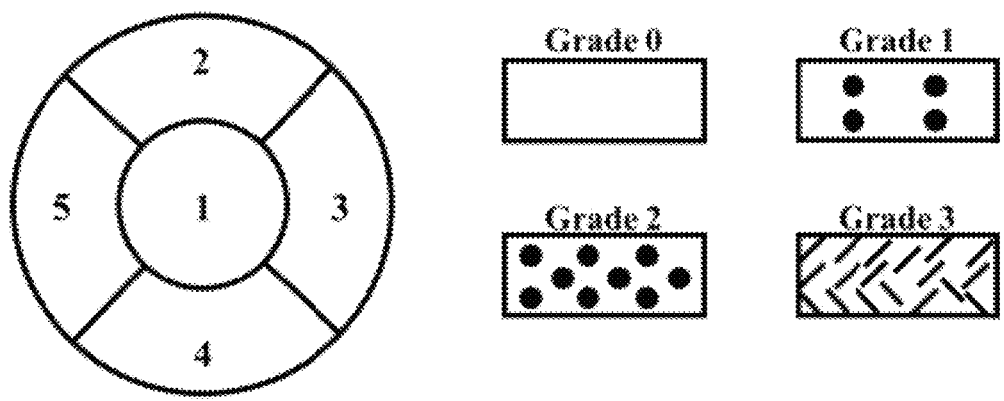
FIG. 5 The diagram of corneal fluorescence staining grading index.

After induction of dry eye symptoms in C57B6/J mice by 0.1% BAC, luciferin staining was applied to the ocular surface of the mice. When the corneal epithelium was intact and uninjured, there was no fluorescence deposition. If the corneal epithelium was in an injured state, luciferin staining would deposit in the injured area, and the green fluorescence will be observed by using a slit lamp to switch to blue light-excited fluorescence. The damaged condition of the corneal epithelium could be observed and scored according to national eye institute grading system (NEI). The cornea was divided into 5 regions and assigned 0 to 3 points according to the severity of green fluorescence deposition. The NEI score was shown as graphic presentation in FIG. 5.

Figure 6:
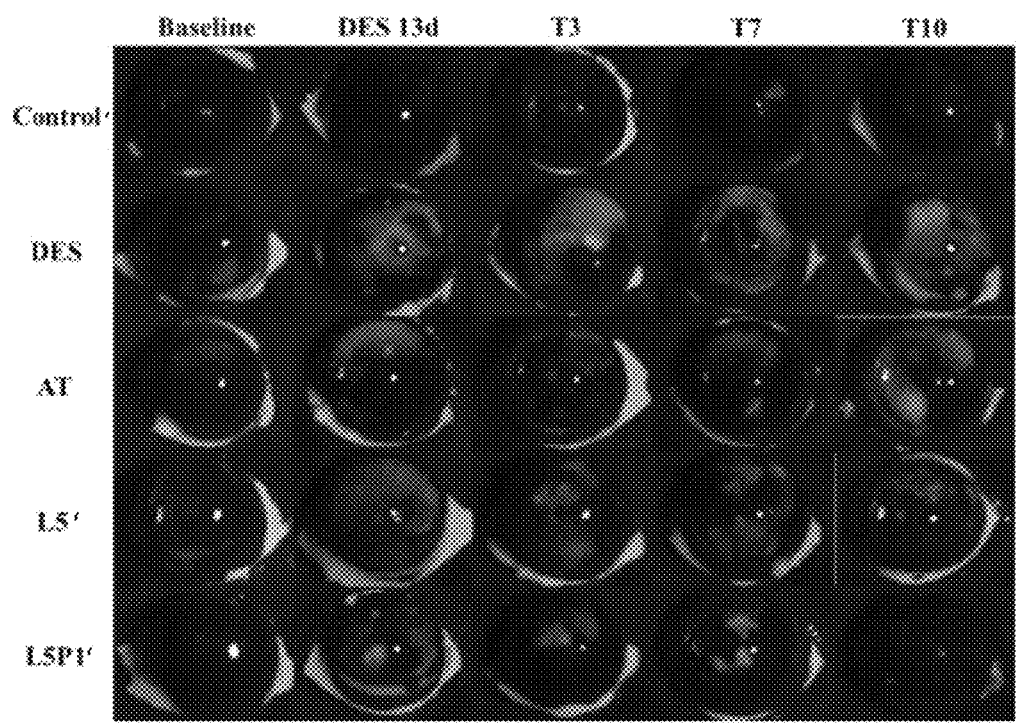
FIG. 6 The result of fluorescence staining of the ophthalmic composition of the present invention for treating dry eye syndrome in mice, and the figure is shown in a color chart.
Figure 7:
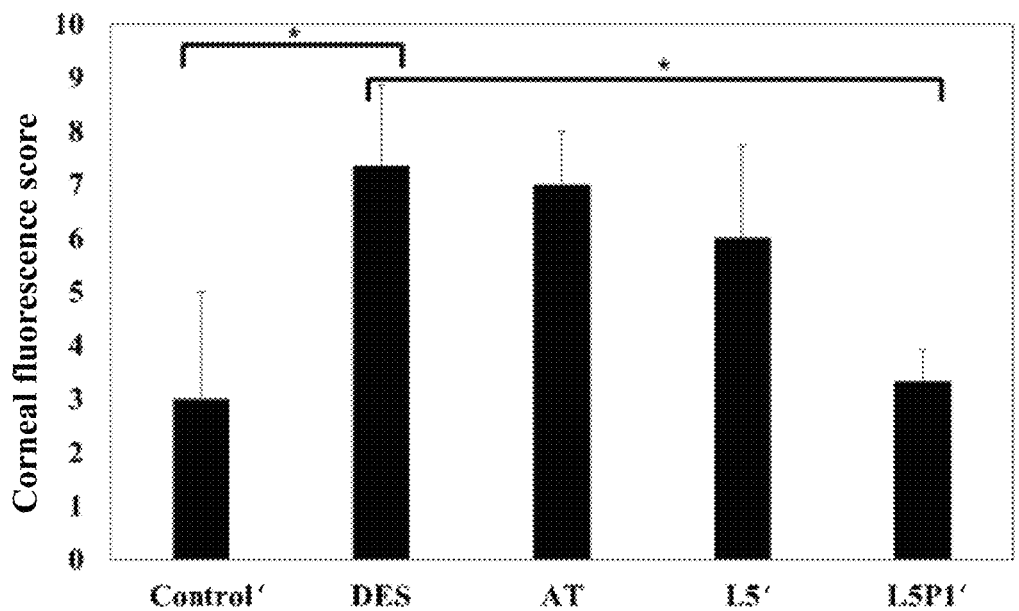
FIG. 7 The quantification of the fluorescence staining on cornea of the ophthalmic composition of the present invention for the treatment of dry eye syndrome mice.

The results were shown in FIGS. 6 and 7, compared with the control group, the corneal epithelium of the dry eye syndrome (DES) group had green fluorescence deposition obviously, indicating that the corneal epithelium was damaged. The mice were treated by AT group, L5' group, L5P1' group for 10 days. After 10 days of treatment, the results showed that there was still obvious green fluorescence deposition in the dry eye syndrome (DES) group. There was no significant improvement in the green fluorescent area after treating by the AT group and the L5' group. However, the L5P1' group showed a decrease in green fluorescence deposition on the cornea after 10 days treatment, indicating that artificial tears mixed with 5 µM lutein and 1% polyvinyl alcohol can repair the cornea injured state. As shown in FIG. 7, the quantification result of corneal fluorescence staining, the staining score of the dry eye group (DES group) was changed after treatment. The fluorescence staining of the corneal epithelial with artificial tears (AT group) treatment was not changed significantly. The fluorescence staining of the corneal epithelial with 5 µM lutein (L5' group) was slightly improved; the fluorescence staining of the corneal epithelial with ophthalmic composition of the present invention (L5P1' group) was significantly improved compared with the dry eye group (DES group), the AT group, and the L5' group.

Figure 8:
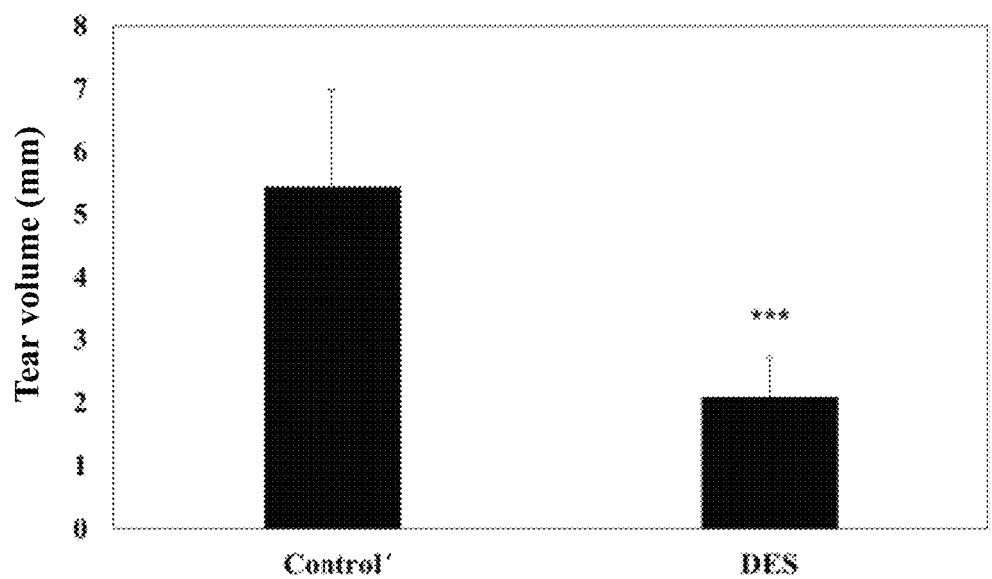
FIG. 8 The result of tears secretion in dry eye syndrome-induced mice.

The abscissa of FIG. 6 was induced-dry eye syndrome (DES) for 13 days; T3 was the third day of treatment; T7 was the 7th day of treatment; T10 was the 10th day of treatment Tear Secretion Test One of the common clinical symptoms of dry eye syndrome was the tears reduction. Therefore, the tear secretion test could also be used as an indicator of whether dry eye syndrome was induced. After 0.1% BAC was treated on the ocular surface of mice for 13 days, the tear amount of dry eye group (DES group) has a significant reduction compared to the control group (FIG. 8).

Figure 9:
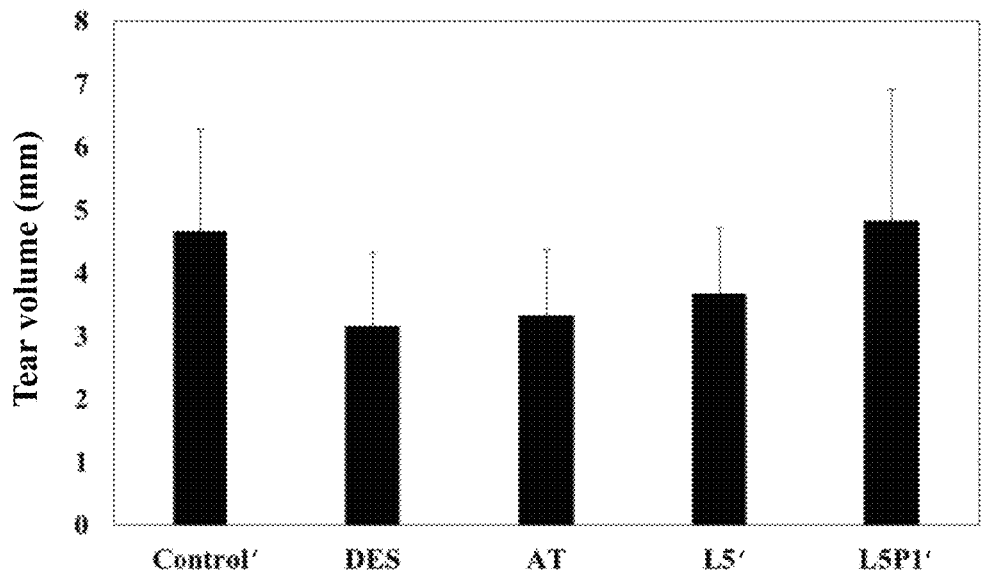
FIG. 9 The result of tears secretion after the treatment of the ophthalmic composition of the present invention in dry eye syndrome mice.

Referring to FIG. 9, the amount of tear secretion of the L5P1' group was restored after the ophthalmic composition of the present invention treatment.

Inflammatory Cytokines Analysis

This example was to test the inflammatory inhibition effect of the ophthalmic composition of the present invention and other groups work on the inflammatory cytokines in dry eye syndrome mice. In this example, the concentrations of inflammatory cytokines such as IL-1β, IL-6 and TNF-α were quantified by ELISA method. The concentration of inflammatory cytokines was changed after 10 days of treatment with the ophthalmic composition of the present invention and other test groups. The tested groups were shown in Table 3.

TABLE 3

The description of variant experimental groups in dry eye syndrome animal study

| Group | Description |
|---|---|
| Control' group | Normal mice with no dry eye syndrome, and no therapeutic drug administered |
| DES group | Mice with dry eye syndrome induced by 0.1% BAC |
| AT group | Mice with dry eye syndrome treated with artificial tears |
| L5' group | Mice with dry eye syndrome treated with 5 µM lutein (L) |
| L5P1' group | Mice with dry eye syndrome treated with 5 µM lutein (L) and 1%(wt./v) PVA |
| C group | Mice with dry eye syndrome treated with a commercially available drug (including Cyclosporine A) |

Figure 10A:
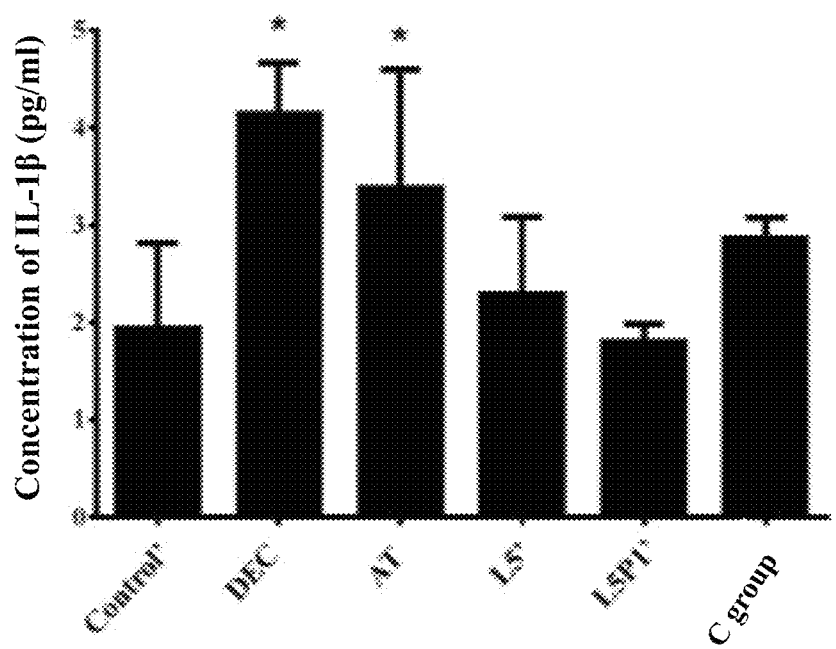
FIG. 10A The concentration of the inflammatory cytokine IL-1β of the corneal lysate treated by the ophthalmic composition of the present invention in animal model.
Figure 10B:
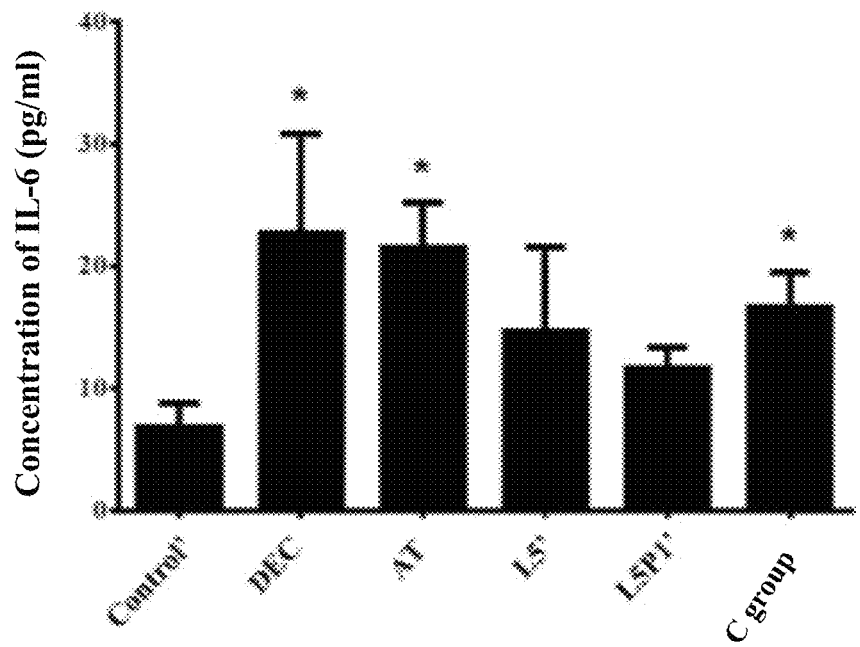
FIG. 10B The concentration of the inflammatory cytokine IL-6 of the corneal lysate treated by the ophthalmic composition of the present invention in animal model.
Figure 10C:
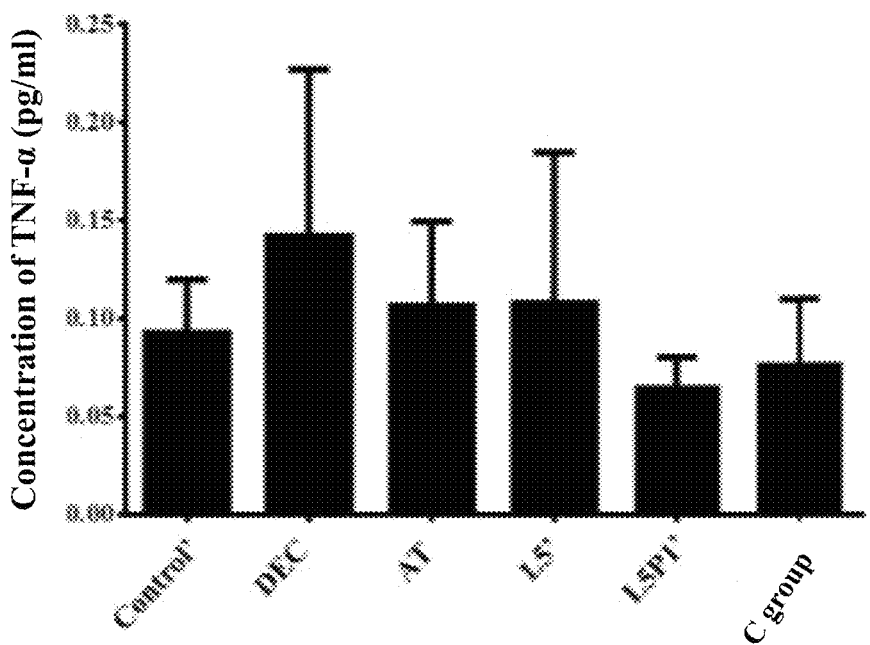
FIG. 10C The concentration of the inflammatory cytokine TNF-α of the corneal lysate of the ophthalmic composition of the present invention in animal model.

As shown in FIGS. 10A to 10C, the inflammatory cytokines in the dry eye syndrome mice (DES group) was increased significantly. The inflammatory cytokines of the L5P1' group was significantly decreased after treated by the ophthalmic composition of the present invention, and indicating that the inflammatory condition of dry eye syndrome was suppressed. The inhibitory effect of the C group was not as good as the present invention. Accordingly, the ophthalmic composition of the present invention was superior to commercial product for inhibiting inflammatory cytokines and relief clinics signs in dry eye syndrome.

The tear secretion test, NEI and corneal fluorescence staining in the foregoing embodiments were conventional techniques; the Non-Invasion In Vivo Image System (IVIS)

was a common instrument, and therefore, it was not described in this specification.

The inventors of the present invention conducted various experiments on the concentration of lutein and polyvinyl alcohol, and the pH value of the ophthalmic composition, wherein the concentration of the lutein ranged from 0.5 μM to 15 μM, and preferably from 2.5 μM to 10 μM in the above examples. The concentration of the polyvinyl alcohol may be ranging from 0.1% to 1.5% (wt./v), and preferably was 1% (wt./v). The pH range of the ophthalmic composition was suitable for normal eye, i.e., pH 6.5 to pH 8.5, preferably, pH 7.7 to pH 8.3.

Without intent to limit the scope of the invention, exemplary instruments, apparatus, methods and their related results according to the embodiments of the present invention are given below. Note that titles or subtitles may be used in the examples for ease, and convenience for people to understand which in no way should limit the scope of the invention.

Symbol Description
- Control group: normal HCE-2 cells, and no drug was added to the medium to cause any changes in the cells.
- LPS control group: cellular inflammation was induced by lipopolysaccharide (LPS), and no drug was added to the medium.
- PVA1 group: 1% (wt./v) polyvinyl alcohol (PVA) was added to the medium.
- L2.5 group: 2.5 μM lutein (L) was added to the medium.
- L5 group: 5 μM lutein (L) was added to the medium.
- L10 group: 10 μM lutein (L) was added to the medium.
- L2.5P1 group: 2.5 μM lutein (L) and 1% (wt./v) polyvinyl alcohol (PVA) were added to the medium.
- L5P1 group: 5 μM lutein (L) and 1% (wt./v) polyvinyl alcohol (PVA) were added to the medium.
- L10P1 group: 10 μM lutein (L) and 1% (wt./v) polyvinyl alcohol (PVA) were added to the medium.
- Control' group: normal mice with no dry eye syndrome, and no therapeutic drug administered.
- DES group: mice with dry eye syndrome induced by 0.1% BAC
- AT group: mice with dry eye syndrome were treated with artificial tears.
- L5' group: mice with dry eye syndrome were treated with 5 μM lutein (L).
- L5P1' group: mice with dry eye syndrome treated with 5 μM lutein (L) and 1% (wt./v) PVA.
- C group: mice with dry eye syndrome were treated with a commercial drug (including Cyclosporine A)

What is claimed is:

1. An ophthalmic composition, comprising lutein, polyvinyl alcohol, and artificial tears, wherein the lutein is present in a concentration of from 1.25 μM to 10 μM, and the polyvinyl alcohol is present in a concentration of from 0.1% to 1.5% (wt./v), and wherein the ophthalmic composition has a pH in a range of from 6.5 to 8.5.

2. The ophthalmic composition of claim 1, wherein the artificial tears comprise sodium chloride, potassium chloride, calcium chloride, and disodium hydrogen phosphate.

3. The ophthalmic composition of claim 1, wherein the concentration of the lutein is from 2.5 μM to 10 μM.

4. The ophthalmic composition of claim 1, wherein the concentration of the polyvinyl alcohol is 1% (wt./v).

5. The ophthalmic composition of claim 1, wherein the pH of the ophthalmic composition is in a range of from 7.7 to 8.3.

6. An ophthalmic composition, comprising lutein, polyvinyl alcohol, and artificial tears, wherein the lutein is present in a concentration of from 2.5 μM to 10 μM, and the polyvinyl alcohol is present in a concentration of from 0.1% to 1.5% (wt./v), and wherein the ophthalmic composition has a pH in a range of from 6.5 to 8.5.

7. The ophthalmic composition of claim 6, wherein the artificial tears comprise sodium chloride, potassium chloride, calcium chloride, and disodium hydrogen phosphate.

8. The ophthalmic composition of claim 6, wherein the concentration of the polyvinyl alcohol is about 1% (wt./v).

9. The ophthalmic composition of claim 6, wherein the pH of the ophthalmic composition is in a range of from 7.7 to 8.3.

* * * * *